United States Patent [19]

Lai et al.

[11] Patent Number: 5,145,982
[45] Date of Patent: Sep. 8, 1992

[54] FUNGICIDAL OXATHIN AZOLES

[75] Inventors: Hoi K. Lai, Guelph, Canada; Robert A. Davis, Cheshire, Conn.

[73] Assignees: Uniroyal Chemical Company, Inc., Middlebury, Conn.; Uniroyal Chemical Ltd./Ltee, Elmira, Canada

[21] Appl. No.: 782,959

[22] Filed: Oct. 25, 1991

Related U.S. Application Data

[62] Division of Ser. No. 566,012, Aug. 10, 1990, Pat. No. 5,081,143, which is a division of Ser. No. 423,821, Oct. 18, 1989, Pat. No. 4,966,910.

[51] Int. Cl.$^5$ .......................................... C07D 411/04
[52] U.S. Cl. ................................ 548/266.2; 548/336
[58] Field of Search ....................... 548/266.2, 336

[56] References Cited

U.S. PATENT DOCUMENTS

| | | | |
|---|---|---|---|
| 3,249,499 | 5/1966 | Von Schmeling et al. | 549/14 |
| 4,152,334 | 5/1979 | Lee | 260/327 M |
| 4,182,716 | 1/1980 | Znotins et al. | 549/14 |
| 4,650,809 | 3/1987 | Bockmann et al. | 514/383 |
| 5,039,332 | 8/1991 | Friedlander et al. | 71/92 |

*Primary Examiner*—Patricia L. Morris
*Attorney, Agent, or Firm*—Glenn E. Karta

[57] ABSTRACT

This invention relates to a novel class of azoles of 5,6-dihydro-1,4-oxathiins having fungicidal activity. The class of compounds is represented by formula (I)

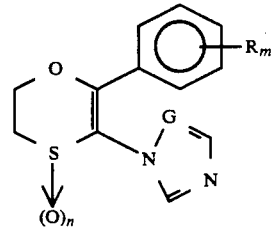

(II)

wherein:
R is each independently halogen; trifluoromethyl; $C_1$-$C_8$ alkyl; $C_3$-$C_6$ cycloalkyl; $C_1$-$C_8$ alkoxy; $C_1$-$C_8$ alkoxycarbonyl; amino; substituted amino; aminocarbonyl; aminosulfonyl; $C_1$-$C_8$ alkoxy sulfonyl; phenyl; phenoxy; phenyl or phenoxy mono-, di- or tri-substituted independently with halogen, trifluoromethyl, $C_1$-$C_8$ alkyl or $C_1$-$C_8$ alkoxy; or benzyl;
G is Ch or N;
m is 0 1 or 2; and
n is 0, 1 or 2.

Fungicidal compositions, methods of controlling fungi and methods for preparing the compounds are within the scope of the invention.

3 Claims, No Drawings

FUNGICIDAL OXATHIN AZOLES

This is a division of applicaton Ser. No. 07/566,012 filed Aug. 10, 1990, now U.S. Pat. No. 5,081,143 which was a division of application Ser. No. 07/423,821 filed Oct. 18, 1989, now U.S. Pat. No. 4,966,910.

BACKGROUND OF THE INVENTION

1. Field of the Invention

The present invention is directed to a class of novel azoles of 5,6-dihydro-1,4-oxathiins and a method for their preparation. More specifically, the present invention is directed to a class of novel azoles of 5,6-dihydro-1,4-oxathiins useful as fungicides.

2. Description of Related Art

The control of phytopathogenic fungi is of great economic importance since fungal growth on plants or on parts of plants, i.e., fruits, blossoms, foliage, stems, tubers, roots, inhibits production of foliage, fruit or seed and the overall quality of the harvested crop.

Plants have long been treated with fungicides to overcome or at least reduce the detrimental effects of fungi. However, the enormous economic toll taken by identified fungi, as well as the development of new fungus strains resistant to known fungicides, establishes a continuing need to develop new and more effective fungicides which possess curative, preventative and systemic action to protect cultivated plants. These new fungicides must not only positively possess these protective properties but, negatively, must not possess properties which have an adverse effect on the plants to be protected.

The use of certain 1,4-oxathiin compounds to Provide fungicidally effective compositions is known in the art. For example, U.S. Pat. No. 3,249,499 described some carboxamido oxathiins as effective biocides, especially systemic fungicides and bactericides. One such compound is 5,6-dihydro-2-methyl-1,4-oxathiin-3-carboxamide as represented by formula (A):

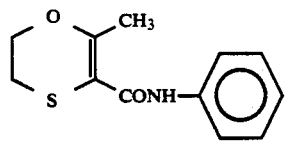
(A)

Also, the use of nitrogen-containing heterocyclic compounds to provide fungicidally effective compositions is known in the art. For example, U.S. Pat. No. 4,202,894 describes a class of heterocyclic compounds, i.e., morpholines, piperidines and the like which are useful as fungicidal agents. Although the compounds of the above discussed prior art disclosures are 1,4-oxathiin and nitrogen-containing heterocyclic compounds, they are characterized by structures which are clearly distinguished from azoles of 5,6-dihydro-1,4-oxathiin.

The rearrangement of 1,3-oxathiolane sulfoxide (B) under acid catalyzed conditions to produce 5,6-dihydro-1,4-oxathiin has been disclosed in U.S. Pat. No. 4,152,334.

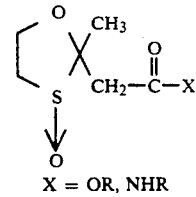
(B)

X = OR, NHR

The rearrangement described in the present invention for azole containing oxathiolane sulfoxides (II) producing novel and fungicidal 5,6-dihydro-1,4-oxathiin-3-azoles (I) has never been disclosed in the literature.

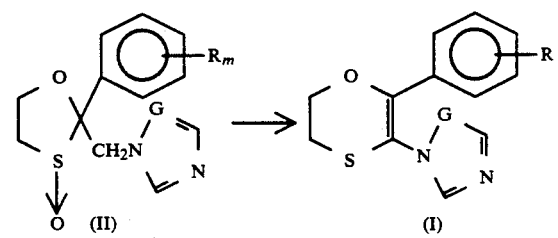

Intermediates (II) and their precursors (III) have been described in EuroPean Patent Publication 0224998 Published Jan. 18, 1989 as having fungicidal properties.

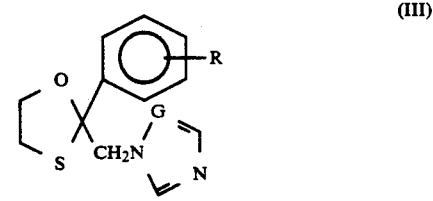
(III)

The above remarks establish that there is recognized a continual need to develop new compounds, distinguished from the comPounds utilized in the prior art, to provide a different spectrum of anti-fungal and/or fungicidal activity against the scourge of phytopathogenic fungi.

SUMMARY OF THE INVENTION

A novel class of azoles of 5,6-dihydro-1,4-oxathiins having a broad sPectrum fungicidal activity; methods for preparing same and fungicidally active compositions containing same are disclosed. The compounds are represented by the formula:

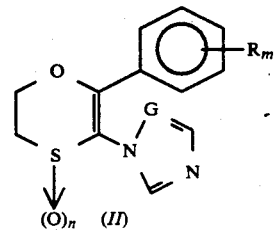
(II)

wherein the substituents R, G, m and n are as hereinafter described.

DETAILED DESCRIPTION OF THE INVENTION

This invention relates to compounds of the formula:

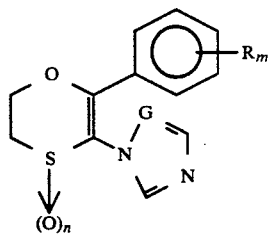
(I)

wherein;

R is each indePendently halogen; trifluoromethyl; $C_1$-$C_8$ alkyl; $C_3$-$C_6$ cycloalkyl; $C_1$-$C_8$ alkoxy;, $C_1$-$C_8$ alkoxycarbonyl; amino; substituted amino; aminocarbonyl; aminosulfonyl; $C_1$-$C_8$ alkoxy- sulfonyl; phenyl; phenoxy; phenyl or phenoxy mono-, di- or tri-substituted independently with halogen, trifluoromethyl, $C_1$-$C_8$ alkyl, or $C_1$-$C_8$ alkoxy; or benzyl;

G is CH or N m is 0, 1 or 2; and n is 0, 1 or 2

Preferably,

R is halogen; $C_1$-$C_4$ alkyl; $C_1$-$C_4$ alkoxy; phenyl; phenoxy; or phenyl or phenoxy mono-substituted with halogen, trifluoromethyl, or $C_1$-$C_4$ alkyl;

G is CH or N;

m is 0 or 1; and n is 0.

In another aspect, this invention relates to fungicidal compositions comprising:

(A) a fungicidally effective amount of a compound having the structure of formula (I) above; and (B) a suitable carrier.

In yet another aspect, this invention relates to a method of controlling fungi, which method comprises applying a fungicidally effective amount of a composition comprised of:

(A) a fungicidally effective amount of a compound having a structure,in accordance with formula (I), and (B) a suitable carrier.

In a further aspect, this invention relates to a process for preparing a compound of the structure:

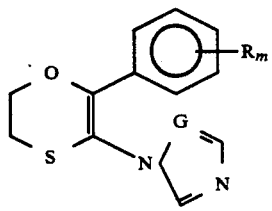
(VII)

wherein R, G and m are as defined in formula (vII) above, which process comprises rearrangement of the corresponding oxathiolane sulfoxide (II) in an inert chlorinated hydrocarbon solvent, such as chloroform or dichloromethane, preferably dichloromethane in the presence of an organic acid such as p-toluene sulfonic acid, preferably methanesulfonic acid at a temperature between 20° C. to 80° C. It is noted that sulfoxide (II) likely exists as a mixture of stereoisomers because of the asymmetric sulfur atom. These stereoisomers are not necessarily separated and can be subjected to rearrangement as a mixture.

The acid catalyzed rearrangement of 1,3-oxathiolane sulfoxides is known in the literature as for example disclosed in U.S. Pat. No. (U.S.P.) 4,152,334. However, this rearrangement reaction has hitherto been unknown for azole containing oxathiolane sulfoxides of formula (II).

Oxathiin sulfoxide (I, n=1) and sulfone (I, n=2) can be prepared by simple oxidation of the initially formed oxathiin (I, n=0). In order to form sulfoxide (I, n=1), the sulfide (I, n=0) is reacted with one equivalent m-chloroperoxybenzoic acid in an inert chlorinated hydrocarbon solvent preferably dichloromethane at between 0° C. to ambient temperature. In order to form sulfone (I, n=2), the sulfide (I,n=0) is reacted with at least two equivalents of m-chloroperoxybenzoic acid in an inert chlorinated hydrocarbon solvent preferably dichloromethane at between ambient to reflux temperature of the solvent.

Compounds of formula (I) form acid addition salts with organic and inorganic acids. The physiologically acceptable salts are also :ntended to be within the scope of this invention.

These salts can be obtained in a simple manner by customary salt-formation methods, for example by dissolving a compound of formula (I) in suitable inert solvent and adding the acid, for example hydrochloric acid, and can be isolated in a known manner, for example by filtration and if appropriate purified by washing with an inert organic solvent.

The synthesis of oxathiolane sulfoxide (II) is illustrated in the following retro-synthetic scheme:

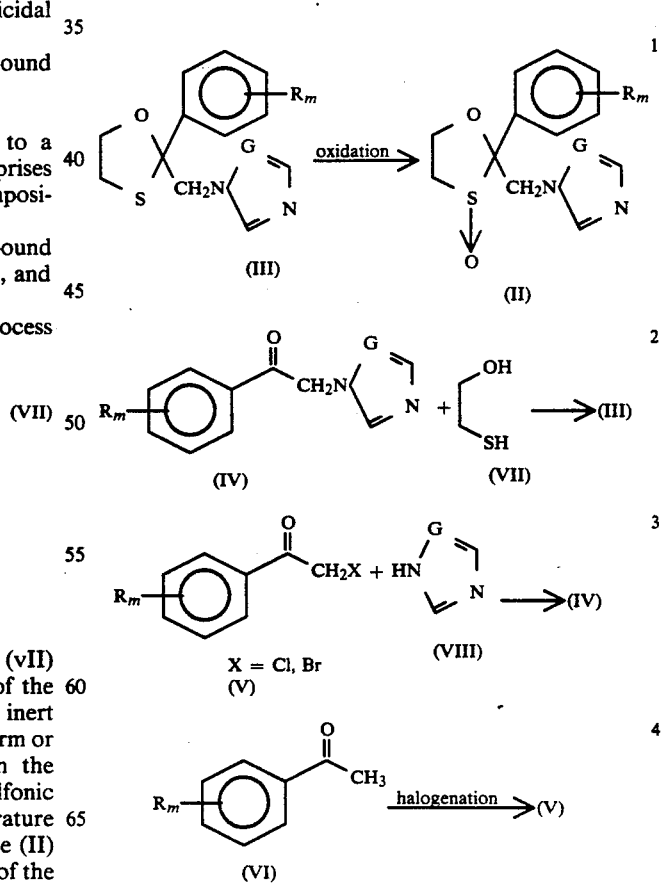

According to Equation 1, sulfoxides of formula (II) are prepared by reacting the oxathiolanes (III) with one equivalent of m-chloroperoxybenzoic acid in an inert chlorinated hydrocarbon solvent Preferably dichloromethane at between 0° C. to ambient temperature.

As shown in Equation 2, oxathiolanes (III) are prepared by reacting the azolylketones (IV) with 2-mercaptoethanol (VII) in the presence of an acid catalyst in a solvent mixture consisting of toluene and 1-butanol and is accompanied by azotropic removal of water under reflux conditions. The preferred catalyst used is p-toluenesulfonic acid or methanesulfonic acid.

Azoyl ketones of formula (IV) are prepared by reacting the corresponding halomethyl ketones (V) with an azole (VIII) by methods disclosed, for example in Canadian Patent No. 1,054,613 and French Patent No. 2,303,475.

Halomethyl ketone of formula (V) and their precursors (VI) are either commercially available or are generally known in the literature and can be prepared according to known procedures by those skilled in the art.

The compounds of formula (I) are useful in a process for controlling phytopathogenic fungi. In this process a fungicidally effective amount of the compound of formula (I) is applied to the locus under attack by said fungi.

In a first preferred embodiment, the method by which a fungicidally effective amount of the compound having structural formula (I) is applied to the plants to be protected from phytopathogenic fungi is by application of the compound to the foliage of the plants to be protected. This compound is applied to the foliage in a concentration of 0.125 to 10 kilograms per hectare (kg/ha); more preferably from 0.125 to 5.0 kg/ha.

In the second preferred embodiment of the process for controlling phytopathogenic fungi, a fungicidally effective amount of the compound having the structural formula (I) is applied to the soil in which the plants to be protected from phytopathogenic fungi are grown. In this embodiment, the compound is applied to the soil at a concentration of 10 to 500 mg/L. The exact dosage, within this concentration range, is dictated by the fungi to be controlled and the particular plants to be protected.

The first preferred embodiment of the process for controlling fungi is known as the foliage method. The second preferred embodiment is known as the systemic method of application. Either method may be utilized prior to infection or after fungi attack has begun.

Alternately, the compound having the structural formula (I) may be applied to seeds as a coating. This method provides plant protection from dangerous fungi by either chemotherapeutic means or systemic means or both. That is, the coating to the seed may protect the soil from infection by the fungi or may be taken up by the plant systematically to protect the plant from the fungal attack. In this seed coating method, the appropriate concentration of the compound is in the range of between 5 and 75 grams of compound per 100 kg. of seed.

The new fungicidal compositions of the present invention comprise a fungicidally effective amount of a compound of formula (I) and a carrier therefor.

The carrier employed in the fungicidal compositions may be a finely divided or granular organic or inorganic inert material. Among the inert carriers within the contemplation of this invention are attapulgate clay, sand, vermiculite, corncobs, activated carbon and mineral silicates, such as mica, talc, pyrophyllite and clays.

In another preferred composition embodiment the carrier comprises a solution. That is, the active agent, a compound of formula (I) is dissolved in a suitable solvent which acts as the carrier. Among the carrier solvents within the contemplation of this invention are acetone, methanol, ispropanol, t-butyl alcohol, cyclohexanone, toluene, xylene, dioxane, dimethylformamide, dimethylsulfoxide, ethylene dichloride, diacetone alcohol, and N-methylpyrrolidone.

In still another preferred carrier embodiment, the carrier comPrises a water emulsion. The water emulsion is prepared from a solution as described immediately above. To the solution is added a surface active agent. Although well-known in the art, a *McCutcheon's Detergents and Emulsifiers*, Allured Publishing Corp., Ridgewood, New Jersey (1970); U.S. Pat. No. 2,514,916, Columns 2 to 4; and U.S. Pat. No. 2,547,734, Columns 3 and 4, provide detailed examples of such surface active agents. The surface active agents may be anionic, non-ionic or cationic.

In still another carrier embodiment, the carrier is a dispersant. In this embodiment, the active agent, i.e., the compound of formula (I), is mixed with a dispersant. The dispersant includes a solvent of the type described above, one of the above-described surface active agents and water. The active agent is dissolved in the solvent to form a solution and the solvent is dispersed in the water with the aid of the surface active agent.

In still another carrier embodiment, the active compound, of formula (I), is premixed with an inert solid carrier which is added to a surface active agent and water to provide another form of dispersion type carrier.

As a variation of the last embodiment, the composition of this invention may take the form of dust, granules or a paste of a wettable powder. In these embodiments, the active compound of formula (I), is admixed with an inert solid carrier to form a solid composition. Thus, for example, in the embodiment wherein a powder is formed, the solid inert carrier is provided in powder form. In many such cases the inert carrier is a mineral silicate. The solid maY be made wettable by the addition of a surface active agent, well known to those skilled in the art, and referred to in the above-recited references directed to surface active agents.

In a final carrier embodiment of the compositions of this invention, the carrier is an aerosol. To prepare an aerosol, the active compound is dissolved in a first solvent. This first solvent is conventional in the sense that although it is volatile it is not highly volatile. This solution is then admixed with a highly volatile solvent, a so-called liquid aerosol carrier. The aerosol carrier is liquid only under elevated pressure. At ordinary temperatures and at atmospheric pressure, the aerosol carrier is a gas. In a sub-embodiment of this preferred carrier, the aerosol carrier may itself be active. For example, the carrier may be an insecticide, a herbicide, a bactericide or the like.

Among the carriers discussed above, the carriers comprising solvents and emulsions are particularly preferred in the Production of the fungicidal compositions of the present invention.

The following examples are given to illustrate the spirit of the present invention. Because these examples are given for illustrative purposes only the invention embodied herein should not be limited to the actual examples provided.

EXAMPLE 1

Preparation of 1-[[2-(4-bromophenyl)-1.3 -oxathiolan-2-yllmethyl]-1(H)-1,2,4-triazole A mixture of 15 g. of 4'-bromo-2-(1H-1,2,4-triazol-1-yl) acetophenone, 13.9 g. 2-mercaptoethanol and 13.9 g. p-toluene-sulfonic acid monohydrate in a solvent mixture consisting of 250 ml toluene and 250 ml 1-butanol was refluxed under Dean-Stark conditions for 72 hours. The reaction was then cooled to allow crystallization of the crude product. The crystals were collected, taken up in dichloromethane and treated with aqueous sodium bicarbonate. The organic extract was dried over sodium sulfate and evaporated to give 8 g. of the desired oxathiolane; m.p.=118°-120° C.

EXAMPLE 2

Preparation of 1-[2-(4-methylphenyl) -1,3-oxathiolan-2-yl] methyl]-1(H)-imidazole A mixture of 20 g. 4'-(methylphenyl)-2-(1(H), imidazole) acetophenone, 31.2 g. 2-mercaptoethanol and 24.7 g. p-toluene-sulfonic acid monohydrate in a solvent mixture consisting of 300 ml of toluene and 300 ml of 1-butanol was refluxed under Dean-Stark conditions for 72 hours. The reaction solution was then concentrated to small volume and the precipitate obtained was treated with 5aqueous sodium hydroxide and extracted with dichloromethane. This extract was dried over sodium sulfate and evaporated to yield 16 g. of the expected oxathiolane; m.p.=86°-89° C.

EXAMPLE 3

Preparption of 1-[[2-(4-bromoohenyl) -1,3-oxathiolan-2-yll ] methyl]-1(H) -1.2.4-triazol, S-oxide A solution of 7.3 g. 1-[[2-(4-bromophenyl) -1,3-oxathiolan-2-yl]-1(H)-1,2,4-triazole in 100 ml dichloromethane at 0° C. was treated with dropwise addition of 4.5 g. m-chloroperoxybenzoic acid in 100 ml dichloromethane. The solution was allowed to warm to room temperature and was stirred overnight. It was then washed with aqueous sodium bicarbonate, dried over sodium sulfate and evaporated to give 7.1 g. of the desired sulfoxide, m.p. - 135°-136° C.

EXAMPLE 4

Preparation of 1-[[2-(4-methylphenyl)-1,3 -oxathiolan-2-yllmethyll-1(H)-imidazole, S-oxide In an analogous manner as described in Example 3, 5 g. of 1-[[2-(4-methylphenyl)-1,3-oxathiolan- 2-yl] methyl]-1(H)-imidazole was oxidized with 3.8 g. of m-chloroperoxybenzoic acid in 75 ml dichloromethane to produce 5 g. of the expected sulfoxide; m.p.=118°-120° C.

EXAMPLE 5

Preparation of 1-2-(4-bromoohenyl)-5,6-dihydro-1,4-oxathiin-3-yl]-1(H)-1,2.4 -triazole (Compound No. 2)

To a solution of 7 g. 1-[[2-(4-bromophenyl) -1,3-oxathiolan-2-yl]methyl]- 1(H)-1,2,4-triazole, S-oxide in 150 ml dichloromethane at room temperature was added 2.6 g. methanesulfonic acid and 2.7 g. acetic anhydride. The mixture was stirred at room temperature overnight then refluxed gently for 2 hours. The solution was then treated with aqueous sodium bicarbonate and the organic layer was dried over sodium sulfate, filtered and evaporated to give a viscous oil. This oil was left standing at ambient temperature to allow crystallization of the product. Re-crystallization with toluene gave 3.1 g. of the titled compound; m.p.=85°-87° C.

EXAMPLE 6

Preparation of 1-[2-(4-bromophenyl)-5,6 -dihydro-1,4-oxathiin-3-yl]-1(H)-imidazole (Compound No. 4)

A mixture of 2.5 g. 1-[[2-(4-methylphenyl)-1,3-oxathiolan-2-yl]methyl]-1(H)-imidazole, 1.2 g. methane- A mixture of 2.5 g 1-[[2-(4-methylphenyl)-1,3-oxathiolan-2yl]methyl]-1(H)-imidazole, 1.2 g. methane sulfonic acid and 1.2 g acetic anhydride in 100 ml dichloromethane was stirred at room temperature overnight. The solution was then washed with aqueous sodium bicarbonate and the organic layer was dried over sodium bicarbonate and the organic layer was dried over sodium sulfate and evaporated to give a solid. Recrystallization with toluene afforded 2.4 g. of the titled compound; m.p.=125°-129° C.

EXAMPLE 7

Preparation of 1-[2-(4-fluorophenyl)-5,6 -dihydro-1,4-oxathiin-3-yl]-1(H)-1,2,4 -triazole. S-oxide (Compound No. 8)

A solution of 2.4 g. m-chloroperoxybenzoic acid in 50 ml dichloromethane was added to a solution of 1.5 g. 1-[2-(4-fluorophenyl)-5,6-dihydro-1,4-oxathiin-3-yl]-1(H)-1,2,4-triazole in 75 ml dichloromethane. After complete addition, the mixture was stirred at room temperature overnight; then brought to reflux for 3 hours. The solution was washed with aqueous sodium bicarbonate, dried over sodium sulfate and evaporated to give 1.5 g. of the desired sulfone; m.p.=195°-197° C.

EXAMPLE 8

Preparation of 1-[2-(3-methoxyphenyl)-5,6 -dihydro-1,4-oxathiin-3-yl]-1(H)-1,2,4 -triazole, hydrochloride Compound No. 27)

In a similar manner as described in Example 5, 1.8 g. of 1-[[2-(3-methoxyphenyl)-1,3-oxathiolan-2-yl]-1(H)-1,2,4-triazole, S-oxide was reacted with 0.8 g. methanesulfonic acid and 0.8 g. acetic anhydride in 50 ml dichloromethane to give an oil identified spectroscopically as 1-[2-(methylphenyl)-5,6-dihydro-1,4-oxathiin-3-yl]-1(H)-1,2,4-triazole.

This oil was dissolved in 150 ml diethylether and treated with a steady stream of hydrogen chloride gas until formation of white precipitates ceased. The precipitates were collected and air-dried yielding 1.6 g. of titled hydrochloride salt; m.p.=132°-136° C.

EXAMPLE 9

Preparation of Compound Nos. 1, 3, 5-7, 9-26 and 28

Additional compounds characterized by structural formula I, wherein R, G, m and n have meanings within the contemplation of the present invention, were prepared in accordance with the procedures enumerated in Examples 1 to 8. These compounds, including their characterizing melting Points or NMR data are summarized in Table I, which appears below. For convenience, the equivalent data for Compound Nos. 2, 4, 8 and 27, formed in accordance with Examples 5-8, respectivley, are also included in Table I.

TABLE I

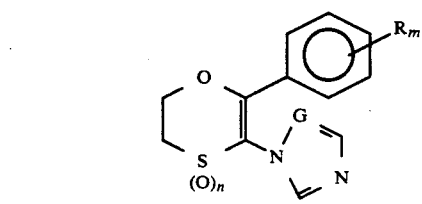

| Cpd. No. | R | m | G | n | M.P. (°C.) |
|---|---|---|---|---|---|
| 1 | 4-phenyl | 1 | N | 0 | 115-117 |
| 2 | 4-Br | 1 | N | 0 | 85-87 |
| 3 | 4-OCH$_3$ | 1 | CH | 0 | 95-97 |
| 4 | 4-CH$_3$ | 1 | CH | 0 | 125-130 |
| 5 | — | 0 | N | 0 | 66-68 |
| 6 | 4-Cl | 1 | N | 0 | 101-105 |
| 7 | — | 0 | N | 2 | 190-192 |
| 8 | 4-F | 1 | N | 2 | 195-197 |
| 9 | 4-phenyl | 1 | N | 2 | 214-217 |
| 10 | 4-(4-Br-phenyl) | 1 | CH | 0 | 178-184 |
| 11 | 4-F | 1 | N | 0 | 132-135 |
| 12 | 4-O-phenyl | 1 | N | 0 | 79-82 |
| 13 | 4-O-(2-Cl-phenyl) | 1 | N | 0 | 105-106 |
| 14 | 4-O-(3-CF$_3$-phenyl) | 1 | N | 0 | 104-106 |
| 15 | 4-O-(3-CH$_3$-phenyl) | 1 | N | 0 | 115-117 |
| 16 | 4-O-(4-F-phenyl) | 1 | N | 0 | 102-104 |
| 17 | 4-O-(3,5-diCH$_3$-phenyl) | 1 | N | 0 | 160-161 |
| 18 | 4-O-(4-CH(CH$_3$)$_2$-phenyl) | 1 | N | 0 | 120-122 |
| 19 | 4-O-(4-C(CH$_3$)$_3$-phenyl) | 1 | N | 0 | 103-105 |
| 20 | 4-O-(2,5-diCH$_3$-phenyl) | 1 | N | 0 | 91-94 |
| 21 | 4-O-(2,4-diCH$_3$-phenyl) | 1 | N | 2 | 147-150 |
| 22 | 4-(CH$_2$)$_4$CH$_3$ | 1 | N | 0 | 73 |
| 23 | 3-F, 4-OCH$_3$ | 2 | HCl-N | 0 | 190 |
| 24 | 3-CH$_3$, 4-CH$_3$ | 2 | N | 0 | 156-159 |
| 25 | 4-OCH$_3$ | 1 | CH | 0 | 95-99 |
| 26 | 3-OCH$_3$, 4-OCH$_3$ | 2 | N | 0 | 133-136 |
| 27 | 3-OCH$_3$ | 1 | HCl.N | 0 | 132-136 |
| 28 | 3-CH$_3$ | 1 | CH | 0 | oil* |

*NMR (CDCl$_3$)δ: 7.7(1H, s), 6.8-7.4(6H, m), 4.5(2H, t), 3.3(2H, t), 2.2(3H, s)

EXAMPLE 10

Preparation of Fungicidal Compositions

The compounds prepared in Examples 5-9 (Compound Nos. 1-28) were formed into compositions. This was accomplished by dissolving 0.3 grams of each of the compounds in 10 ml of acetone or other suitable inert solvent. Each of these solutions were treated with 1 to 2 drops of an emulsifying agent, such as Triton X-100, a trademark of Rohm & Haas for an octyl phenoxy polyethoxy ethanol, and water was added to form an emulsion. The degree of dilution with water was dictated by the desired concentration of the composition. The greater the quantity of water added the lower the concentration of the composition, reported in milligrams per liter (mg/1).

EXAMPLE 11

Control of Powdery Mildew Fungus (Systemic Root Uptake)

Each of the Compound Nos. 1-28 prepared in accordance with Examples 5-9 were tested to evaluate their effectiveness in preventing or controlling powdery mildew disease of barley caused by the fungus *Erysiphe graminis* and powdery mildew disease of cucumber caused by the fungus, *Erysiphe cichoracearum*. This prevention or control capability was tested by utilizing the compounds of the present invention to control these diseases by systemic root uptake.

To accomplish this task, pots (4×4×3.5 inches) containing 10 plants of barley (Variety "Herta") and cucumber (Variety "Marketmore 70") were grown to age 6 days and 10 days, respectively. Upon reaching these ages, 45 ml of emulsion compositions formed in accordance with Example 10 were added to each pot. That is, 48 pots were treated with emulsion compositions of the 28 compounds prepared in accordance with Examples 5-9. The 45 ml compositions saturated the soil without significant loss through drainage into the saucers below the pots. In addition, a number of pots containing the same barley and cucumber plants were left untreated. These pots were used as controls.

Twenty-four hours after the treatment with the compositions of the present invention, both the barley and cucumber plants in all the pots, those treated and those untreated, were inoculated with powdery mildew fungus. This was accomplished by tapping leaves of previously infected barley and cucumber plants over the treated and untreated pots containing the barley and cucumber plants, respectively, to distribute spores of the fungus over the plants tested.

Six days after inoculation, disease control was evaluated on a 0 to 6 rating scale. A 0 rating was assigned when no disease was evidenced and a 6 rating was given for severe disease. Intermediate ratings were assigned depending on the degree of disease. Percent control was computed by comparing the ratings for the treated and untreated plants.

The results of this example, that is, the percent control for each of the compounds tested is reported in Table II. The results of the powdery mildew disease control of barley is reported under the title of "CMS 250". It is noted that Table II appears after Example 17.

EXAMPLE 12

Control of Powdery Mildew in Barley by Foliar Application

Eight plants of "Larker" variety barley were planted in a pot. The number of pots were sufficient to accomodate testing in duplicate or triplicate pots for each of the 28 compounds tabulated in Table I. This number included a duplicate number of pots which acted as controls as will be discussed below.

Each of the compounds tabulated in Table I were tested by being sprayed onto the plants as compositions, prepared in accordance with Example 10 at an emulsion composition concentration of 1,000 mg/1. Compositions of each compound were sprayed on two or three pots. A number of pots were unsprayed and thus acted as controls. That is, for each pot sprayed, an unsprayed pot was utilized as a control.

After the leaves of the sprayed pots were dried, they and the unsprayed control pots were placed in a greenhouse maintained at 21° C. All the pots were then inoculated with barley powdery mildew fungus, *Erysiphe graminis*. This inoculation was accomplished by distributing spores of the fungus over the leaves to be tested from plants which had previously been infected with the mildew disease.

Five days after inoculation, the plants were evaluated and assigned a disease rating of 0 to 5 as described in Example 11. Again, percent control was computed by comparing the treatment scores with the scores of the untreated controls. The results of these tests are summarized in Table II under the title "BMP 1000".

EXAMPLE 13

Control of Rice Balst Disease by Foliar Treatment

Five Bellemont rice plants each were grown in a plurality of pots. The number of pots with planted rice plants were sufficient to test the compositions of all compounds listed in Table I as well as controls therefor, the number of controls equal to the number of pots treated with each compound.

Three to four weeks after planting, the rice plants were sprayed with compositions of the compounds of this invention, prepared in accordance with Example 10. The concentration of each composition was 1,000 mg/1. An equal number of pots, also containing five rice plants per pot, remained unsprayed.

Sprayed and unsprayed pots of the plant were inoculated with spores of the rice blast fungus, *Pyricularia oryzae*. This inoculation was accomplished by preparing inoculum containing 20,000 to 30,000 spores per milliliter. The inoculum so prepared was sprayed on the plants with 1 to 2 drops of Tween 20, a trademark of I.C.I. for a non-ionic surfactant (ethoxylated ethylene sorbitan monolaurate) to insure proper wetting of the inoculum onto the plant leaves.

The plants were incubated in a controlled chamber at a humidity of 99% and a temperature of 21° C. for about 24 hours to allow infection to occur. The plants, after 24 hours in the control chamber, were transferred to a greenhouse for six days to permit disease development to occur. Disease was manifested by blast lesions on the leaves. Disease control was calculated by either counting lesions, if infection was moderate, or evaluating by the 0 to 6 rating system defined in Example 11. Of course, the evaluation system used in rating any of the compounds of the present invention was also utilized in evaluating its control. The results of this test are also tabulated in Table II under the title "RCB 1000".

EXAMPLE 14

Control of Bean Rust Fungus Eradicant Test

Pots were planted with two pinto bean plants, *P. vulgaris* each, susceptible to rust disease. When the plants were 7 days old, at the primary leaf stage of growth, they were all sprayed with a susPension containing 20,000 spores of the bean rust fungus, *Uromyces phaseoli*, per ml. All the pots containing the plants were then incubated in a controlled environmental chamber, maintained at 99% humidity and 21° C., for 24 hours to allow infection to occur. The plants were then removed from the incubator and allowed to dry. Two days after inoculation the infected plants were sprayed with compositions formed from the compounds of this invention, set forth in Example 10, at a dosage of 1,000 mg/l. A number of infected plants were not sprayed and acted as controls. All of the sprayed and unsprayed plants were then placed in a greenhouse at 21° C. for five days to allow any disease present to be expressed.

All the plants sprayed with the spore suspension were assessed for disease using the 0 to 6 rating system described in Example 11. Control of disease was determined by comparing treated plants with the untreated controls. The control of disease, expressed as percent reduction of disease, is included in Table II under the title "BRE 1000".

EXAMPLE 15

Control of Peanut Cercospora Leafspot by Foliar Treatment

Four Virginia peanut plants were grown in each of a plurality of pots. Enough pots were prepared so that the four plants in each of the pots could be sprayed with each of the compounds listed in Table I. This spraying occured when the plants reached 4 weeks old. The 28 compounds of this invention were aPPlied to the peanut plants by spraying emulsion compositions, prepared in accordance with the method employed in Example 10. The concentration of the emulsion compositions were 900 mg/l for each of the compounds listed in Table I. A number of pots containing four 4-week old Virginia peanut plants were left untreated to act as controls.

The treated (sprayed) and control (unsprayed) plants, after drying, were inoculated with spores of Peanut Cercospora leafspot, *Circospora arachidicola*. The inoculum contained 20,000 to 30,000 spores per ml. The inoculum was sprayed with 1 to 2 drops of Tween 20 surfactant to aid in wetting the leaves with the inoculum. All the inoculated peanut plant pots were incubated in a temperature-humidity control chamber at 24° C. for 36 hours to develop infection. The plants were then placed in a greenhouse for 21 days to allow disease development.

After 21 days in the greenhouse, all the plants were evaluated on the 0 to 6 disease rating system. Percent control was comPuted by comparing the scores of the treated pots and the untreated control pots. The results of this test are summarized in Table II under the title "PNT 900".

EXAMPLE 16

Control of Barley Blast

Pots were prepared such that they included 10 plants of 6-day old barley "Herta" variety. These pots were sprayed with compositions, formulated in accordance with the procedure of Example 10 of the compounds set forth in Table I. These pots, and a number of control pots planted with 10 "Herta" variety barley plants which were unsprayed, were inoculated with spores of the blast fungus, *Pyricularia oryzae*. In that *Pyricularia oryzae* is the same fungus utilized in Example 13, the method of inoculation was in accordance with the description given in that example.

All the inoculated pots were placed in a greenhouse maintained at a temperature of 21° C. and a humidity of 99% for five days. At that time, the plants were evaluated using the 0 to 6 disease rating scale. percent control was computed by comparing the treatment scores of the treated and untreated pots. The results of this test are included in Table II under the title "BBL 1000".

EXAMPLE 17

Control of Nine Fugus Species

Compounds listed in Table I were solubilized in acetone at a concentration of 500 mg/l. That is, solutions were made of the compounds of the present invention such that there was 500 parts by weight of active compounds per million parts by volume of acetone. Filter paper discs, each 11 mm. diameter, were dipped in each of the test solutions. The discs were allowed to air dry to drive off the acetone solvent. A number of discs were treated to provide controls.

The treated and untreated discs were then placed on agar plates and 8 fungus species: *Alternaria slani* (ALT), *Botrytis cinerea* (BOT), *Fusarium oxysporum* (FUS), *Helminthosporium maydis* (HMAY), *Phytophthora infestans* (PHY), *Erysiphe polgoni* (PMP), Sclerotinia sclerotiorum (SCM) and *Sclerotium rolfsii* (SCO) were added to the center of each test disc in the form of a culture plug with the fungus mat in contact with the treated paper of the test disc. Two drops of a ninth fungi species, *Cercospora arachidicola* (CER), were added as spore suspension (20,000 spores/ml) to the chemically treated test disc, rather than a mycelial culture plug. The plates were incubated at 29° C. in an oven and then the first eight fungus species were evaluated by measuring the radius from the center of the fungus colony of the untreated discs.

Percent growth inhibition of each of the compounds tested was determined as a function of the difference between the radii of the treated and untreated disc for these eight fungus species.

In the case of the *Cercospora arachidicola* (CER) fungi, scoring was done on a numerical bases as follows:
100=Complete inhibition of germination and growth.
80=Nearly complete inhibition but some growth.
50=Partial inhibition of growth or, early complete inhibition but later growth begins.
20=Some inhibition of growth, but not significant.
0=No inhibition of growth.

The results of all the above tests appear in Table II under the titles "ALT 500," "BOT 500," "FUS 500," "HMAY 500," "PHY 500," "PMP 1000," "SCM 500," "SCO 500" and "CER 500."

TABLE II

| Cpd. No. | ALT 500 | BBL 1000 | BMP 1000 | BMS 250 | BOT 500 | BRE 1000 | CER 500 | CMS 250 | FUS 500 | HMAY 500 | PHY 500 | PMP 1000 | PNT 900 | RCB 1000 | SCM 500 | SCO 500 |
|---|---|---|---|---|---|---|---|---|---|---|---|---|---|---|---|---|
| 1 | 100 | 50 | 100 | 0 | 85 | 50 | 100 | 0 | 25 | 100 | 45 | 0 | — | — | 35 | 0 |
| 2 | 0 | — | — | 0 | 100 | — | 0 | 20 | 25 | 50 | 50 | — | — | — | 35 | 50 |
| 3 | 40 | 100 | 100 | 15 | 65 | 98 | 50 | 50 | 55 | 60 | 100 | 0 | — | 38 | 0 | 15 |
| 4 | 60 | 20 | 100 | 0 | 0 | 0 | 100 | 0 | 20 | 60 | 100 | 90 | — | — | 15 | 0 |
| 5 | 35 | 40 | 20 | 100 | 0 | 0 | 0 | 80 | 50 | 0 | 40 | 50 | — | — | 0 | 0 |
| 6 | 25 | 60 | 100 | 100 | 50 | 90 | 0 | 100 | 25 | 15 | 100 | 95 | — | — | 25 | 65 |
| 7 | 25 | 60 | 15 | 20 | 0 | 0 | 0 | 15 | 0 | 0 | 10 | 0 | — | — | 0 | 15 |
| 8 | 25 | 40 | 15 | 0 | 25 | 0 | 0 | 15 | 0 | 0 | 0 | 0 | — | — | 15 | 40 |
| 9 | 45 | 60 | 65 | 20 | 35 | 0 | 0 | 35 | 15 | 0 | 30 | 0 | — | — | 20 | 30 |
| 10 | 55 | 60 | 90 | 0 | 10 | 100 | 100 | 35 | 50 | 35 | 100 | 30 | 50 | — | 0 | 25 |
| 11 | 0 | 90 | 50 | 100 | 35 | 0 | 0 | 100 | 15 | 35 | 65 | 60 | — | — | 20 | 35 |
| 12 | 65 | 100 | 100 | 0 | 0 | 75 | 100 | 15 | 25 | 100 | 50 | 50 | — | 33 | 30 | 0 |
| 13 | 35 | 100 | 100 | 15 | 0 | 65 | 50 | 0 | 50 | 75 | 75 | 20 | — | — | 35 | 0 |
| 14 | 35 | 100 | 100 | 0 | 0 | 25 | 0 | 15 | 20 | 15 | 50 | 0 | — | — | 25 | 0 |
| 15 | 25 | 80 | 90 | 15 | 0 | 15 | 0 | 15 | 20 | 40 | 75 | 0 | — | — | 25 | 0 |
| 16 | 35 | 80 | 100 | 0 | 0 | 80 | 50 | 0 | 20 | 45 | 50 | 0 | — | — | 30 | 0 |
| 17 | 35 | 60 | 20 | 15 | 0 | 0 | 0 | 15 | 40 | 0 | 20 | 0 | — | — | 0 | 0 |
| 18 | 35 | 100 | 40 | 0 | 0 | 0 | 0 | 35 | 0 | 0 | 0 | 0 | — | — | 0 | 0 |
| 19 | 0 | 90 | 100 | 0 | 0 | 0 | 0 | 15 | 0 | 100 | 0 | 0 | — | — | 0 | 0 |
| 20 | 35 | 60 | 50 | 0 | 0 | 0 | 0 | 0 | 15 | 25 | 60 | 0 | — | — | 10 | 0 |
| 21 | 0 | 20 | 0 | 0 | 0 | 0 | 0 | 0 | 0 | 25 | 35 | 0 | — | — | 0 | 0 |
| 22 | 50 | 65 | 35 | 0 | 0 | 0 | 0 | 15 | 45 | 65 | 60 | 0 | — | — | 0 | 15 |
| 23 | 0 | 0 | 65 | 100 | 15 | 0 | 0 | 100 | 0 | 0 | 50 | 0 | — | — | 0 | 25 |
| 24 | 0 | 0 | 35 | 0 | 0 | 0 | 0 | 0 | 0 | 0 | 0 | 0 | — | — | 0 | 35 |
| 25 | 35 | 0 | 0 | 0 | 65 | 0 | 50 | 0 | 0 | 100 | 100 | 0 | — | — | 10 | 50 |
| 26 | 0 | 0 | 15 | 0 | 0 | 0 | 0 | 0 | 0 | 0 | 0 | 0 | — | — | 0 | 40 |
| 27 | 5 | 0 | 0 | 85 | 0 | 0 | 0 | 85 | 0 | 25 | 50 | 0 | — | — | 5 | 35 |
| 28 | 35 | 90 | 100 | 100 | 35 | 0 | 50 | 85 | 100 | 55 | 100 | 0 | — | — | 0 | 35 |

EXAMPLE 18

Comparative Examples

Comparative tests using the procedures heretofore described, were preformed with compounds analogous to those of the instant invention to determine the biological efficacy of the analogue. The compound and associated results are reported in Table III. These compounds are outside the scope of this invention.

TABLE III

| Comparative Compound | ALT 500 | FUS 500 | BMS 250 | BRE 1000 | PMP 1000 | RCB 1000 | SCM 500 |
|---|---|---|---|---|---|---|---|
| 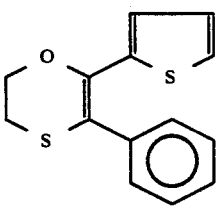 | 45 | 60 | 0 | 0 | — | — | — |
| 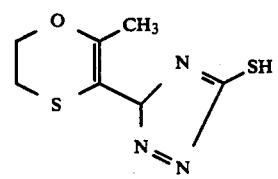 | 15 | — | — | 0 | 0 | 5 | 0 |
| 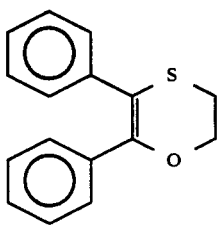 | 40 | 40 | 0 | 0 | — | — | — |

TABLE III-continued

| Comparative Compound | ALT 500 | FUS 500 | BMS 250 | BRE 1000 | PMP 1000 | RCB 1000 | SCM 500 |
|---|---|---|---|---|---|---|---|
| 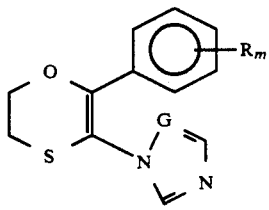 | 15 | 70 | 0 | 0 | — | — | — |
| 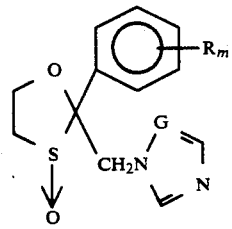 | 0 | 0 | — | 0 | 0 | — | 0 |

We claim:

1. The process of preparing a compound of formula VII:

(VII)

wherein:
R is each independently halogen; trifluoromethyl; $C_1-C_8$ alkyl; $C_3-C_6$ cycloalkyl; $C_1-C_8$ alkoxy; $C_1-C_8$ alkoxycarbonyl; amino; aminocarbonyl; aminosulfonyl; $C_1-C_8$ alkoxysulfonyl; phenyl; phenoxy; phenyl or phenoxy mono-, di- or tri-substituted independently with halogen, trifluoromethyl, $C_1-C_8$ alkyl or $C_1-C_8$ alkoxy; or benzyl;
G is CH or N; and
m is 0, 1 or 2:
comprising
i) reactively rearranging a compound of formula II (II)

wherein: R, G and m are as defined above in the presence of an inert chlorinated hydrocarbon solvent and an organic acid at from 20° C. to 80° C.; and
ii) isolating the compound of formula VII from the reaction mixture.

2. The process of claim 1 wherein:
R is halogen; $C_1-C_4$ alkyl; $C_1-C_4$ alkoxy; phenyl; phenoxy; or phenyl or phenoxy mono-substituted with halogen, trifluoromethyl, or $C_1-C_4$ alkyl;
G is CH or N; and
m is 0 or 1.

3. The process of claim 1 wherein the inert chlorinated hydrocarbon is dichloromethane and the organic acid is methanesulfonic acid.

* * * * *